(12) United States Patent
Dreux et al.

(10) Patent No.: US 10,035,739 B2
(45) Date of Patent: Jul. 31, 2018

(54) PROCESS FOR THE PRODUCTION OF HIGH-PURITY PARAXYLENE FROM A XYLENES CUT, USING TWO SIMULATED MOVING BED SEPARATION UNITS OPERATING IN SERIES AND TWO ISOMERIZATION UNITS

(71) Applicant: IFP Energies nouvelles, Rueil-Malmaison (FR)

(72) Inventors: Heloise Dreux, Lyons (FR); Philibert Leflaive, Mions (FR); Damien Leinekugel Le Cocq, Oullins (FR)

(73) Assignee: IFP Energies nouvelles, Rueil-Malmaison (FR)

( * ) Notice: Subject to any disclaimer, the term of this patent is extended or adjusted under 35 U.S.C. 154(b) by 0 days.

(21) Appl. No.: 15/326,836

(22) PCT Filed: Jun. 10, 2015

(86) PCT No.: PCT/EP2015/062981
§ 371 (c)(1),
(2) Date: Jan. 17, 2017

(87) PCT Pub. No.: WO2016/008652
PCT Pub. Date: Jan. 21, 2016

(65) Prior Publication Data
US 2017/0210682 A1 Jul. 27, 2017

(30) Foreign Application Priority Data

Jul. 18, 2014 (FR) .................................... 14 56940

(51) Int. Cl.
C07C 5/27 (2006.01)

(52) U.S. Cl.
CPC .......... *C07C 5/2737* (2013.01); *C07C 5/2775* (2013.01); *C07C 2529/40* (2013.01); *C07C 2529/74* (2013.01)

(58) Field of Classification Search
CPC . C07C 5/2737; C07C 5/2775; C07C 2529/40; C07C 2529/74
See application file for complete search history.

(56) References Cited

U.S. PATENT DOCUMENTS

2008/0262282 A1 10/2008 Leflaive et al.
2014/0155667 A1 6/2014 Ou et al.

FOREIGN PATENT DOCUMENTS

FR 2862638 A1 5/2005

OTHER PUBLICATIONS

International Search Report dated Aug. 18, 2015, issued in corresponding PCT/EP2015/062981, 2 pages.
English translation Abstract of FR2862638A1 published May 27, 2005 (1 page).

*Primary Examiner* — Brian A McCaig
*Assistant Examiner* — Jason Y Chong
(74) *Attorney, Agent, or Firm* — Millen, White, Zelano and Branigan, P.C.

(57) ABSTRACT

The present invention describes a process for the production of high-purity paraxylene from a xylenes cut capable of containing ethylbenzene and C9 compounds, said process using two simulated moving bed separation units operating in series and two isomerization units.

20 Claims, 3 Drawing Sheets

PROCESS FOR THE PRODUCTION OF HIGH-PURITY PARAXYLENE FROM A XYLENES CUT, USING TWO SIMULATED MOVING BED SEPARATION UNITS OPERATING IN SERIES AND TWO ISOMERIZATION UNITS

FIELD OF THE INVENTION

Paraxylene production has been steadily increasing for thirty years. Paraxylene is used for the production of terephthalic acid and polyethylene terephthalate resins, in order to provide synthetic textiles, bottles, and plastic materials more generally.

In order to satisfy the ever-increasing demand for paraxylene, petrochemists have a choice between increasing the capacity of existing units (called debottlenecking in the remainder of the text), or constructing new units.

The present invention makes it possible to respond to these two hypothetical cases, and more particularly the debottlenecking of existing units, as the modifications involved are relatively small.

In the remainder of the text reference will be made to the simulated moving bed separation unit (abbreviation SMB) or separation unit (SMB). A separation unit (SMB) may contain one or more adsorbers.

EXAMINATION OF THE PRIOR ART

The production of high-purity paraxylene by separation by adsorption is well known from the prior art. Industrially, this operation is carried out within a sequence of processes called "C8 aromatic loop". This "C8 aromatic loop" includes a stage of elimination of the heavy compounds (i.e. having more than 9 carbon atoms, denoted C9+) in a distillation column called "xylenes column".

The top flow of this column, which contains the C8 aromatic isomers, is then sent to the process for the separation of paraxylene, which is generally a process of separation by adsorption in a simulated moving bed.

The extract which contains the paraxylene is then distilled by means of an extraction column, then a toluene column, in order to obtain paraxylene of high purity.

The raffinate, rich in metaxylene, orthoxylene and ethylbenzene, after a stage of elimination of the solvent by distillation, is treated in a catalytic isomerization unit which returns a mixture of C8 aromatics, in which the proportion of xylenes (ortho-, meta-, para-xylenes) is practically at thermodynamic equilibrium, and the quantity of ethylbenzene reduced. This mixture is again sent to the "xylenes column" with the fresh feedstock.

The prior art proposes numerous variants of this basic layout implementing one or more separation units (by adsorption, crystallization, distillation or using a membrane) and/or one or more gas-phase isomerization units (converting ethylbenzene by isomerization to xylenes or by dealkylation to benzene), or liquid-phase (not converting ethylbenzene).

In particular, patent FR2862638 describes a process for the production of paraxylene from a hydrocarbons feedstock, in an adsorption column with simulated moving bed operation, having at least five zones and delivering an extract, a raffinate-2 and an intermediate raffinate. The raffinate-2 is sent to an isomerization unit operating preferentially in liquid phase and at a low temperature. The intermediate raffinate having a content enriched with ethylbenzene is isomerized in vapour phase.

Alternatively, U.S. Pat. No. 8,273,934 describes a process for the production of paraxylene comprising:
(a) separating a feedstock containing C8 hydrocarbons in order to produce a flow rich in C8 hydrocarbons,
(b) separating a first part of the flow rich in C8 hydrocarbons in order to produce a first flow rich in paraxylene and a first raffinate low in paraxylene,
(c) isomerizing at least a part of the raffinate in order to obtain an isomerate,
(b) separating a second part of the flow rich in C8 hydrocarbons in order to produce a second flow rich in paraxylene and a second raffinate low in paraxylene,
(e) in liquid phase, at least partially isomerizing at least a part of the second raffinate in order to produce an isomerate,
(f) recovering at least a part of at least one of the two flows rich in paraxylene in order to produce high-purity paraxylene by means of a separation by adsorption,
(g) sending at least a part of the first isomerate and at least a part of the second isomerate to the separation unit (a).

It should be noted that when the paraxylene separation unit is a process of separation by adsorption, the C9+ content in the feedstock must be very low (typically less than several hundred ppm by weight) so as to avoid the accumulation of these compounds in the solvent recycling loop. Thus industrially and in the aforementioned patents, there is systematically a treatment of at least a part of the feedstock supplying the separation unit(s) by adsorption or by distillation with a very strict specification of the C9-aromatics content. Now, this separation is very energy-intensive. A need therefore exists to optimize the sequence of processes within the C8 aromatic loop so as to limit the operating costs, in particular those linked to the separation of C9 aromatics. Such issues also arise during the remodelling of existing units so as to increase the quantity of paraxylene produced. This operation is called debottlenecking, a term that will be used in the remainder of the text.

Thus it is a question of minimizing the costs of investment linked to the modifications to be made to the C8 aromatic loop, as well as the operating costs of the functioning of the sequence of processes after remodelling.

The present invention uses two SMB adsorption separation units and two isomerization units, combined with the injection of the fresh feedstock into a single one of the two separations by adsorption. It makes it possible to limit or even to eliminate the treatment of the feedstock upstream of one of the separation units, unlike the solutions proposed by the prior art.

Using two separation units by SMB adsorption makes it possible in addition to treat more feedstock than the sequence proposed in patent FR2862638, which makes it possible to maximize the use of high performance new generation adsorbent and to meet the current requirements for paraxylene production greater than 1 million tonnes annually on a single site. Making common use of the columns downstream of the two units for separation by adsorption also ensures that multiple distillation columns are not required and thus minimizes the investment. This also allows optimum use of the existing distillation columns in the case of the remodelling of an existing separation unit with 24 beds in two 12-bed separation units. Finally, mixing the two intermediate raffinates (enriched with ethylbenzene) originating from the two units for separation by adsorption allows the optimization of the EB conversion in the gas-phase isomerization.

In the remainder of the text, by separation unit is meant simulated moving bed separation units; by adsorbers is meant assemblies of beds of adsorbent, a unit being capable of containing one or more adsorbers.

By isomerization unit and distillation columns is meant the other items of equipment of the process.

BRIEF DESCRIPTION OF THE INVENTION

Figure 1:
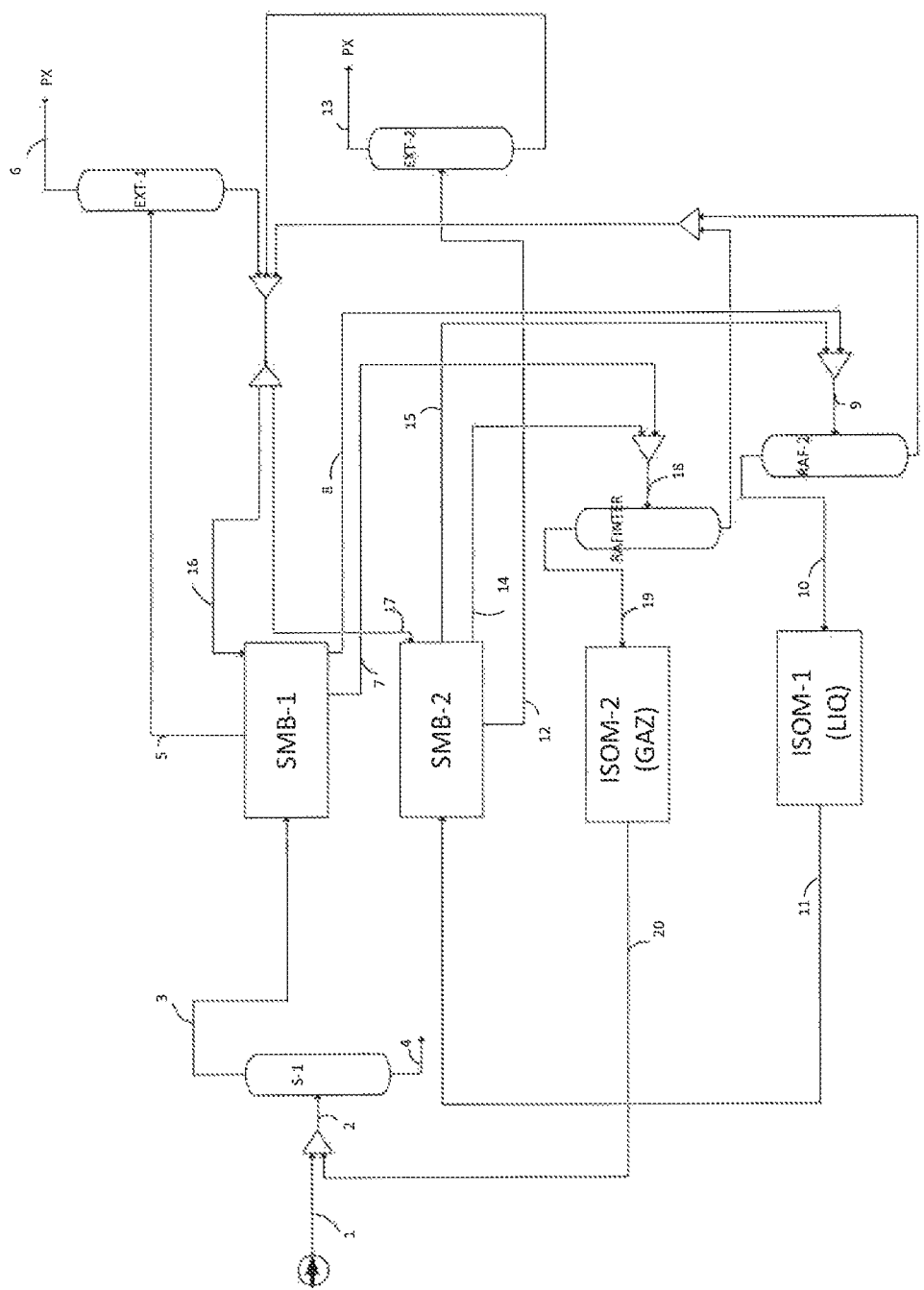
FIG. 1 shows the layout of the process according to the present invention with the two moving bed separation units denoted SMB-1 and SMB-2 and the two isomerization units denoted ISOM-1 and ISOM-2.

The present invention can be defined as a process for the production of high-purity paraxylene from a xylenes cut, containing ethylbenzene and C9+ compounds, a process using two simulated moving bed separation units (SMB-1 and SMB-2) operating in series, and two isomerization units (ISOM-1 et ISOM-2).

By operation in series of the simulated moving bed separation units (SMB-1 et SMB-2), is meant that the effluent from the separation unit (SMB-1) is used indirectly as a feedstock for the separation unit (SMB-2), indirectly meaning that separation units or isomerization units can be arranged alternately on the path of the effluent from the separation unit (SMB-1).

More specifically, the process according to the present invention consists of the following series of stages:
the feedstock (2) is sent to a distillation column (S-1) from where a mixture (3) is drawn off at the top comprising the major part of the metaxylene, paraxylene, ethylbenzene, and at least a part of the orthoxylene, and from where a flow (4) of C9-C10 hydrocarbons and the remaining part of the orthoxylene is drawn off at the bottom.
the mixture from the top (3) is separated in the separation unit (SMB-1) including at least one adsorber containing a plurality of interconnected beds and operating in a closed loop, said adsorber comprising at least five zones delimited by the injections of the flow (3) and of the desorbent (16), and a first extract (5) containing paraxylene, a first intermediate raffinate (7) containing ethylbenzene, and a first raffinate-2 (8) containing orthoxylene and metaxylene are drawn off,
the isomerate (11) originating from the isomerization unit (ISOM-1) is separated in the separation unit (SMB-2), said separation unit (SMB-2) being constituted by at least one adsorber containing a plurality of interconnected beds and operating preferentially in a closed loop, and said separation unit comprising at least five zones delimited by the injections of the flow (11) and of the desorbent (17), and a second extract (12) containing paraxylene, a second intermediate raffinate (14) containing ethylbenzene, and a second raffinate-2 (15) containing orthoxylene and metaxylene are drawn off,
the first extract (5) originating from the column (SMB-1) is distilled in a column (EXT-1), in order to recover a first fraction (6) enriched with paraxylene,
the two raffinates-2, flows (8) and (15), are mixed in order to form the flow (9) which is distilled in a column (RAF-2) so as to substantially eliminate all the desorbent and in order to draw off a first distilled fraction (10).
a first isomerization unit (ISOM-1) is supplied with the flow (10), in order to obtain the first isomerate (11),
the two intermediate raffinates, flows (7) and (14) are mixed in order to form the flow (18) which is distilled in a column (RAFINTER) in order to eliminate substantially all of the desorbent and in order to draw off a second distilled fraction (19),
a second isomerization unit (ISOM-2) is supplied with the flow (19), in order to obtain a second isomerate (20), which is recycled to the inlet of the separation column (S-1).

The present invention can have several variants, some of which are described below.

All these variants are compatible with one another.

According to a variant of the process for the production of high-purity paraxylene according to the invention,
the first extract (5) originating from the separation unit (SMB-1) is distilled in a column (EXT-1), in order to recover a first fraction (6) enriched with paraxylene,
the second extract (12) is distilled in a column (EXT-2), in order to recover a second fraction (13) enriched with paraxylene.

In another variant of the process for the production of high-purity paraxylene according to the invention, the two extracts (5) and (12) are distilled in a single common extraction column in order to recover a single fraction enriched with paraxylene.

According to a preferred variant of the process for the production of high-purity paraxylene according to the invention, the isomerization unit (ISOM1) operates in liquid phase under the following conditions:
Temperature less than 300° C., preferably comprised between 200 and 260° C.,
Pressure less than 4 MPa, preferably comprised between 2 and 3 MPa,
Space velocity less than 10 $h^{-1}$, preferably comprised between 2 $h^{-1}$ and 4 $h^{-1}$,
Catalyst comprising at least one zeolite having channels the opening of which is defined by a ring with 10 or 12 oxygen atoms (10 MR or 12 MR), preferentially a catalyst comprising at least one zeolite having channels the opening of which is defined by a ring with 10 oxygen atoms (10 MR), and even more preferably, a catalyst comprising a zeolite of the ZSM-5 type.

According to another variant of the process for the production of high-purity paraxylene according to the invention, the isomerization unit (ISOM-2) operates in gas phase under the following conditions:
temperature greater than 300° C., preferably from 360° C. to 480° C.,
pressure less than 2.5 MPa and preferably from 0.5 to 0.8 MPa,
hourly space velocity less than 10 $h^{-1}$, preferably comprised between 0.5 $h^{-1}$ and 6 $h^{-1}$,
hydrogen to hydrocarbon molar ratio less than 10, and preferably comprised between 3 and 6.

According to another variant of the process for the production of high-purity paraxylene according to the invention, the catalyst used for the isomerization unit ISOM-2 contains an acid zeolite, for example of the MFI, MOR, MAZ, MTW, FAU and/or EUO structure type and, preferably, contains a zeolite of the EUO structure type, and at least one metal of group VIII of the periodic table.

According to another variant of the process for the production of high-purity paraxylene according to the invention, the catalyst used for the isomerization unit ISOM-2 comprises at least one zeolite having channels the opening of which is defined by a ring with 10 to 12 oxygen atoms (10 MR or 12 MR), and at least one group VIII metal at a content comprised between 0.1 and 0.3% by weight, inclusive.

According to another variant of the process for the production of high-purity paraxylene according to the invention, the separation unit (SMB1) uses PDEB as a desorbent.

In a variant of the process according to the present invention, the separation unit (SMB-2) uses toluene as a desorbent.

In a variant of the process according to the present invention, the separation units (SMB1) and (SMB2) contain from 6 to 24 beds, and preferably from 8 to 15 beds, distributed over one or more adsorbers, the number of beds being adjusted so that each bed preferably has a height comprised between 0.70 m and 1.40 m.

In another variant of the process according to the present invention, the distribution of the quantity of solid adsorbent in the separation units (SMB-1) and (SMB-2) is as follows:
the quantity of solid adsorbent in zone 1 is 16%±5%,
the quantity of solid adsorbent in zone 2 is 40%±5%,
the quantity of solid adsorbent in zone 3A is 16%±5%,
the quantity of solid adsorbent in zone 3B is 16%±5%,
the quantity of solid adsorbent in zone 4 is 12%±5%, In another variant of the process for the production of high-purity paraxylene according to the invention, the ratio by volume of desorbent to feedstock is at least 1.7/1 and preferably comprised between 1.5/1 and 0.4/1, inclusive.

In another variant of the process for the production of high-purity paraxylene according to the present invention, the ratio of the flow rates of intermediate raffinate and of raffinate-2 is comprised between 0.3/1 and 5/1, and preferably comprised between 0.4/1 and 1/1, inclusive.

In another variant of the process for the production of high-purity paraxylene according to the invention, for the separation unit (SMB-2), the ratio by volume of desorbent to feedstock is at least 1.7/1 and preferably comprised between 1.5/1 and 0.4/1, inclusive.

In another variant of the process for the production of high-purity paraxylene from a xylenes cut containing ethylbenzene and C9+ compounds according to claim 1, in which for the separation unit (SMB-2), the ratio of the flow rates of intermediate raffinate and of raffinate-2 is comprised between 0.3/1 and 5/1, and preferably comprised between 0.4/1 and 1/1, inclusive.

In another variant of the process for the production of high-purity paraxylene according to the invention, the debottlenecking of an existing separation unit, constituted by two adsorbers in series, can be carried out as follows:
the last bed of the first adsorber is connected to the first bed of the first adsorber via a line containing at least one recirculation pump, this first adsorber acting as a separation unit (SMB-1)
the last bed of the second adsorber is connected to the first bed of the second adsorber via a line containing at least one recirculation pump, this second adsorber acting as a separation unit (SMB-2)

In general, the configuration of the two adsorbers can have a fixed number of beds in each of the adsorbers, or have a fixed number of beds in one of the adsorbers and variable in the other, or variable for both adsorbers.

Preferably, the two adsorbers have a fixed number of beds in each of the chromatographic zones.

Finally, in another variant of the process for the production of high-purity paraxylene according to the invention, the configuration of the two simulated moving bed adsorbers has a fixed number of beds in each of the chromatographic zones of each of the two adsorbers.

DETAILED DESCRIPTION OF THE INVENTION

The feedstock (2) is sent to a distillation column (S-1) from where a mixture (3) the major part comprising metaxylene, paraxylene, ethylbenzene, and at least a part orthoxylene is drawn off at the top, and from where a flow (4) of C9-C10 hydrocarbons and the remaining part of the orthoxylene is drawn off at the bottom.

A first separation is carried out of the top mixture (3) in the separation unit (SMB-1) constituted by a plurality of interconnected beds and operating in a closed loop, said separation unit comprising at least five zones delimited by the injections of the flow (3) constituting the first feedstock of the column and of the desorbent (16), and a first extract (5) containing paraxylene, a first intermediate raffinate (7) containing ethylbenzene, and a first raffinate-2 (8) containing orthoxylene and metaxylene are drawn off, The five zones of the separation unit (SMB-1) are as follows:
zone 1 comprised between the injection of the desorbent (16) and the draw-off of the extract (5),
zone 2 comprised between the draw-off of the extract (5) and the injection of the feedstock (3),
zone 3A comprised between the injection of the feedstock (3) and the draw-off of the intermediate raffinate (7),
zone 3B comprised between the injection of the intermediate raffinate (7) and the draw-off of the raffinate-2 (8),
zone 4 comprised between the draw-off of the raffinate-2 (8) and the injection of the desorbent (16), A second simulated moving bed separation (SMB-2) is carried out of the isomerate (11) originating from the isomerization unit (ISOM-1), from which optionally all or part of the heavy C9 and C10 compounds have been removed by distillation (either in a dedicated column, or in the column S-1). Preferably, the isomerate (11) is sent to the simulated moving bed separation unit (SMB-2) without an intermediate stage of elimination of the C9+ compounds. The separation unit (SMB-2) is constituted by a plurality of beds that are interconnected and operating in a closed loop, said separation unit comprising at least five zones delimited by the injections of the flow (11) constituting the second feedstock of the column and of the desorbent (17), and the draw-offs of a second extract (12) containing paraxylene, a first intermediate raffinate (14) containing ethylbenzene, and a second raffinate-2 (15) containing orthoxylene and metaxylene.

The five zones of the separation unit (SMB-2) are as follows:
zone 1 comprised between the injection of the desorbent (17) and the draw-off of the extract (12),
zone 2 comprised between the draw-off of the extract (12) and the injection of the second feedstock (11),
zone 3A comprised between the injection of the second feedstock (11) and the draw-off of the intermediate raffinate (14),
zone 3B comprised between the draw-off of the second intermediate raffinate (14) and the draw-off of the second raffinate-2 (15),
zone 4 comprised between the draw-off of the raffinate-2 (15) and the injection of the desorbent (17), Preferentially, a first extract (5) is distilled in a distillation column (EXT-1), in order to recover a first fraction (6) enriched with paraxylene, Preferentially, a second extract (12) is distilled in a distillation column (EXT-2), in order to recover a second fraction (13) enriched with paraxylene. The two extracts (5) and (12) can also be distilled in a single common extraction column in order to recover a single fraction enriched with paraxylene.

The two raffinates-2, flows (8) and (15), are preferentially mixed in order to form the flow (9) which is distilled in a distillation column (RAF-2) in order to substantially eliminate all the desorbent and in order to draw off a first distilled fraction (9) low in ethylbenzene.

The two raffinates-2 flows (8) and (15) can also be distilled in two different columns, then the two distilled fractions low in ethylbenzene are mixed. The distilled fraction(s) obtained supply(supplies) a first isomerization unit (ISOM-1) in order to obtain a first isomerate (11) preferentially supplying the separation unit (SMB-2), but capable of being partially recycled at the inlet of the distillation column (S-1).

the two intermediate raffinates, flows (7) and (14) are preferentially mixed in order to form the flow (18) and distilled in a column (RAFINTER) in order to substantially eliminate all of the desorbent and in order to draw off a second distilled fraction (19) rich in ethylbenzene.

The two intermediate raffinates flows (7) and (14) can also be distilled in two different columns, then the two distilled fractions low in ethylbenzene are mixed. The distilled fraction(s) obtained feed(s) a second isomerization unit (ISOM-2), in order to obtain a second isomerate (20), recycled to the inlet of the separation column (S-1).

The first isomerization unit (ISOM-1) operating preferably in liquid phase, is generally operated under the following conditions:

Temperature less than 300° C., preferably 200° C. to 260° C.,

Pressure less than 4 MPa, preferably 2 to 3 MPa

Hourly space velocity (HSV) less than 10 h$^{-1}$ (10 liters per liter per hour), preferably comprised between 2 and 4 h$^{-1}$, Catalyst including at least one zeolite having channels the opening of which is defined by a ring with 10 or 12 oxygen atoms (10 MR or 12 MR), preferentially a catalyst including at least one zeolite having channels the opening of which is defined by a ring with 10 oxygen atoms (10 MR), and even more preferably, a catalyst including a zeolite of ZSM-5 type.

The second isomerization unit (ISOM-2) operating in gas phase, is generally operated under the following conditions:

Temperature greater than 300° C., preferably 350° C. to 480° C.

Pressure less than 4 MPa, preferably comprised between 0.5 and 2 MPa

Hourly space velocity (HSV) less than 10 h$^{-1}$ (10 liters per liter per hour), preferably comprised between 0.5 and 6 h$^{-1}$, Catalyst including at least one zeolite having channels the opening of which is defined by a ring with 10 or 12 oxygen atoms (10 MR or 12 MR), preferentially a catalyst comprising a zeolite of the EUO, MTW or MOR structure type, and at least one group VIII metal, $H_2$/hydrocarbons molar ratio less than 10, and preferably comprised between 3 and 6.

The catalyst of the gas-phase isomerization unit (ISOM-2) can comprise a zeolite of the EUO, MTW or MOR structure type, and at least one metal of group VIII of the periodic table in a proportion by weight of 0.01% to 2% with respect to the catalyst. The catalyst of the gas-phase isomerization unit (ISOM-2) can in certain cases contain an EU-1 zeolite and platinum.

The desorbents used in the simulated moving bed separation units (SMB-1 and SMB-2) are generally selected from paradiethylbenzene, toluene, paradifluorobenzene or diethylbenzenes in a mixture.

The ratio by volume of the desorbent to the feedstock in the simulated moving bed separation units (SMB-1 and SMB-2) is comprised between 0.5 and 2.5, and preferably comprised between 0.8 and 2.

The simulated moving bed separation units (SMB-1 and SMB-2) are operated at a temperature comprised between 20° C. and 250° C., preferably between 90° C. and 210° C., and even more preferably between 140° C. and 180° C., and under a pressure comprised between the bubble pressure of xylenes at the operating temperature and 2 MPa.

The ethylene content of the second distilled fraction originating from the raffinate-2 (flows (8) and (14)) is less than that of the feedstock and preferably reaches at most 10% by weight.

The operation of the process according to the invention, and in particular the composition of the different flows, is detailed hereinafter with reference to FIG. 1.

The fresh feedstock is introduced through the line (1) into a distillation column (S-1). This fresh feedstock contains mainly C8-aromatic compounds, xylenes and ethylbenzene, in a variable proportion according to the origin of the cut. It can possibly contain impurities in a variable quantity depending on the origin of the feedstock which will be essentially C9 and C10 aromatic compounds and paraffinic and naphthenic compounds.

The content of naphthenic or paraffinic compounds is advantageously less than 1% by weight. Preferably, this content is less than 0.3% by weight, and even more preferably this content is less than 0.1% by weight.

The feedstock can originate either from a reforming unit, or from a toluene disproportionation unit, or from a unit for the transalkylation of toluene and C9 aromatics.

An isomerate conveyed by a line (20) is added to the fresh feedstock.

The bottom effluent (4) from the column (S-1) is essentially constituted by C9 and C10 aromatic compounds, and optionally orthoxylene.

Optionally, the mixture (4) of orthoxylene and C9-C10 aromatic hydrocarbons drawn off at the bottom of the distillation column (S-1), can be sent to another distillation column from which a high-purity orthoxylene flow (at least 98.5%) is extracted at the top, and a flow containing C9-C10 hydrocarbons at the bottom.

The top effluent (3) from the column (S-1), constitutes the feedstock of a simulated moving bed separation unit (SMB-1). The simulated moving bed separation unit (SMB-1) is supplied on the one hand with the feedstock conveyed by the line (3), and on the other hand with the desorbent conveyed by a line (16).

Any type of desorbent can be used. The preferred desorbent is paradiethylbenzene, however other desorbents such as toluene, paradiethylbenzene or diethylbenzenes in a mixture can also be suitable.

The effluents from the (SMB-1) unit are an extract (5), an intermediate raffinate (7) and a raffinate-2 denoted (8), said separation unit comprising at least five zones delimited by the injections of feedstock and of desorbent, and the draw-offs of raffinate-2 and of extract.

The total number of beds of the separation unit (SMB-1) according to the invention is preferably comprised between 6 and 24 beds, and even more preferably between 8 and 15 beds distributed over one or more adsorbers.

The number of beds will be adjusted so that each bed preferably has a height comprised between 0.70 m and 1.40 m.

The distribution of the quantity of solid adsorbent in each zone is as follows:
the quantity of solid adsorbent in zone 1 is 16%±5%,
the quantity of solid adsorbent in zone 2 is 40%±5%,
the quantity of solid adsorbent in zone 3A is 16%±5%,
the quantity of solid adsorbent in zone 3B is 16%±5%,
the quantity of solid adsorbent in zone 4 is 12%±5%, According to a preferred characteristic of the invention, it is possible to inject the desorbent and the feedstock into the separation unit (SMB-1), in a ratio by volume of desorbent to feedstock of at most 1.7/1 and preferably comprised between 1.5/1 and 0.4/1, inclusive.

According to a preferred characteristic of the invention, the ratio of the flow rates of intermediate raffinate and of raffinate-2 is comprised between 0.3/1 and 5/1, inclusive, and preferably between 0.4/1 and 1/1 inclusive.

The extract (5) is essentially constituted by toluene, paraxylene and desorbent.

The intermediate extract (7) is essentially constituted by toluene, metaxylene and orthoxylene, ethylbenzene, paraxylene for the part not recovered in the extract, and desorbent.

The raffinate-2 (8) is essentially constituted by metaxylene and orthoxylene and desorbent. It is substantially free from paraxylene and depleted of ethylbenzene. The extract (5) is sent to a distillation column (EXT-1).

From the distillation column (EXT-1), the desorbent which is sent back to the separation unit (SMB-1) is drawn off through the line (16), and a mixture of paraxylene and toluene through the line (6).

The raffinate-2 (8) is sent to a distillation column (RAF-2).

From the distillation column (RAF-2) desorbent which is sent back to the line (16), and a mixture of metaxylene and orthoxylene through a line (9), which is sent to the isomerization unit (ISOM-1), are drawn off.

The isomerization unit (ISOM-1) preferentially in liquid phase, operates preferentially under the following conditions:
temperature less than 300° C., preferably comprised between 200 and 260° C.,
pressure less than 4 MPa, preferably comprised between 2 and 3 MPa,
hourly space velocity less than 10 $h^{-1}$, preferably comprised between 2 $h^{-1}$ and 4 $h^{-1}$, All the catalysts capable of isomerizing hydrocarbons with 8 carbon atoms are suitable for the isomerization unit (ISOM-2) of the present invention. Preferably, a catalyst containing a zeolite of type ZSM-5 is used.

The effluent from the isomerization unit (ISOM-1) is sent back through the line (11), either to the distillation column (S-1), or directly to the inlet of the separation unit (SMB-2) in the case where the content of compounds other than the C8 aromatics is very low, typically of the order of 1% by weight. The C9 content is typically less than 1000 ppm by weight.

Any type of desorbent can be used. The preferred desorbent is paradiethylbenzene, however other desorbents such as toluene, paradiethylbenzene or diethylbenzenes in a mixture can also be suitable.

The effluents from the separation unit (SMB-2) are an extract (12), an intermediate raffinate (14) and a raffinate-2 (15), said separation unit comprising at least five zones delimited by the injections of feedstock and desorbent, and the draw-offs of intermediate raffinate, raffinate-2 and extract. The total number of beds of the separation unit (SMB-2) according to the invention is preferably comprised between 6 and 24 beds, and even more preferably comprised between 8 and 15 beds distributed over one or more adsorbers.

The number of beds will be adjusted so that each bed preferably has a height comprised between 0.70 m and 1.40 m.

The distribution of the quantity of solid adsorbent in each zone is as follows:
the quantity of solid adsorbent in zone 1 is 16%±5%,
the quantity of solid adsorbent in zone 2 is 40%±5%,
the quantity of solid adsorbent in zone 3A is 16%±5%,
the quantity of solid adsorbent in zone 3B is 16%±5%,
the quantity of solid adsorbent in zone 4 is 12%±5%, According to another preferred characteristic of the invention, it is possible to inject the desorbent and the feedstock into the separation unit (SMB-2), in a ratio by volume of desorbent to feedstock of at most 1.7/1 and preferably comprised between 1.5/1 and 0.4/1, inclusive.

According to a preferred characteristic of the invention, the ratio of the flows of intermediate raffinate and of raffinate-2 is comprised between 0.3/1 and 5/1, inclusive, and preferably between 0.4/1 and 1/1 inclusive.

The configuration (average number of beds per zone) of the two simulated moving bed units (SMB-1 and SMB-2) can be:
having a fixed number of beds in each of the chromatographic zones (mode known as "simulated moving bed" as defined in patent FR 2 976 501),
having a variable number of beds for one adsorber ("VARICOL" mode as defined in the patent FR 2 976 501) and a fixed number for the other,
having a variable number of beds for both adsorbers.

The extract (12) is essentially constituted by toluene, paraxylene and desorbent.

The intermediate extract (14) is essentially constituted by toluene, metaxylene and orthoxylene, ethylbenzene, paraxylene with respect to the part not recovered in the extract, and desorbent.

The raffinate-2 (15) is essentially constituted by metaxylene and orthoxylene and desorbent. It is substantially free from paraxylene and depleted of ethylbenzene. The extract (12) is sent to a distillation column (EXT-2).

From the distillation column (EXT-2), the desorbent which is sent back to the zone 1 of the column (SMB-2) is drawn off through the line (17), and a mixture of paraxylene and toluene through the line (13).

The intermediate raffinate is sent through a line (14) with the intermediate raffinate (7) into the distillation column (RAFINTER). From the distillation column (RAFINTER) desorbent which is sent back through the line (17) into the separation unit (SMB-2), and a mixture of xylenes and ethylbenzene through a line (19), are drawn off. The effluents of the line (19) are sent to the isomerization unit (ISOM-2) operating at a high temperature in vapour phase.

The isomerization unit (ISOM-2) is preferably operated under the following conditions:
temperature greater than 300° C., preferably from 360° C. to 480° C.,
pressure less than 2.5 MPa and preferably from 0.5 to 0.8 MPa, hourly space velocity less than 10 h$^{-1}$, preferably comprised between 0.5 h$^{-1}$ and 6 h$^{-1}$, hydrogen to hydrocarbon molar ratio less than 10, and preferably comprised between 3 and 6.

All the catalysts capable of isomerizing the hydrocarbons with 8 carbon atoms, zeolitic or not, are suitable for the isomerization unit (ISOM-2) of the present invention. Preferably, a catalyst containing an acid zeolite, for example of the MFI, MOR, MAZ, FAU and/or EUO structure type is used. Even more preferably, a catalyst is used containing a zeolite of the EUO structure type and at least one metal from group VIII of the periodic table.

Preferably, the catalyst of the isomerization unit (ISOM-2) includes from 1 to 70% by weight of a zeolite of the EUO structure type (EU-1 for example) comprising silicon and at least one element T preferably selected from aluminium and boron, the Si/T ratio of which is comprised between 5 and 100. Said zeolite is at least partially in the form of hydrogen, and the sodium content is such that the Na/T atomic ratio is less than 0.1. Optionally the catalyst of the isomerization unit can contain between 0.01 and 2% by weight of tin or indium, and sulphur at a content of 0.5 to 2 atoms per atom of the group VIII metal.

The effluent of the isomerization unit (ISOM-2) is sent into a separation system which makes it possible to recover a part of the hydrogen which is recycled to the isomerization unit (ISOM-2). The non-recycled part of the hydrogen is made up by an addition of fresh hydrogen. At the end of the separation system an isomerate constituted by the heaviest fractions is recovered, which is sent back to the distillation column (S-1) through the line (20).

The process according to the invention is particularly suitable for a modification to an existing unit for the purpose of increasing the quantity of paraxylene produced; an operation that is known as debottlenecking.

In the case of debottlenecking an existing aromatic loop, the invention consists of significantly increasing the flow of fresh feedstock and the flow of paraxylene produced, while continuing to use the main equipment of the loop, i.e.:
1) the xylenes distillation column (S-1)
2) the simulated moving bed xylenes separation unit, typically operating as 24 beds
3) the isomerization unit (ISOM-2) supplied with the raffinate drawn off from the separation column converting the ethylbenzene using for example a catalyst based on zeolite of the EUO structure type comprising a reactor, a recycling compressor, a stabilization column and a column allowing the C8 and C9 naphthenes to be recovered so as to recycle them to the feedstock,
4) the raffinate column (RAFINTER)
5) the extract column (EXT-1)

In order to carry out this debottlenecking according to the invention, a 24-bed simulated moving bed containing two 12-bed adsorbers in series is converted to a process with two twelve-bed adsorbers, each connected in parallel. To this end:

The twelfth bed of the first adsorber is connected to the first bed of said first adsorber via a line containing at least one recirculation pump, the twelfth bed of the second adsorber is connected to the first bed of said second adsorber via a line containing at least one recirculation pump.

The system controlling and regulating the flow rates of injection of the feedstock and of the desorbent and the draw off flow rates of the extract and of the raffinate of the 24-bed adsorption stage is adapted so as to be able to manage the injection and draw-off flow rates independently in each of the two adsorbers of the remodelled process according to the invention.

For the injection devices, this operation can be carried out either by doubling the pump+measurement device system in order to regulate the flow rate injected into each of the adsorbers, or, with the aim of minimizing costs, by using the pre-existing pump and measurement device which will manage the two flows to be injected as a whole, and by adding a system for the measurement and regulation of the flow rate supplying one of the two adsorbers.

When the supply or the draw off of the fluids over all of the plates of the existing 24-bed process is ensured by a plurality of on-off controlled valves, there are no additional modifications to be made to the supply and draw-off networks.

When the supply or the draw off of the fluids over all of the plates of the existing 24-bed process is ensured by the use of a multi-way rotary valve, these functions will preferably be ensured by the use of two multi-way rotary valves 15 (optionally reusing the pre-existing valve on one of the two ways after adaptation).

In the case of an existing 24-bed unit constituted by twice twelve beds in series, the main flow circulates from the bottom of the first adsorber to the top of the second adsorber, and from the bottom of the second adsorber to the top of the first adsorber.

The flows originating from the bottoms of the two adsorbers are then redirected to circulate to the top of the adsorber from which they originated by carrying out modifications to the valves and pipes. The bottom flow of the first adsorber is recycled to the top of said adsorber and the bottom flow of the second adsorber is recycled to the top of said adsorber.

The configuration (average number of beds per zone) of the two adsorbers can be according to one of the 3 variants disclosed above, i.e.:

Having a fixed number of beds in each of the chromatographic zones for the two absorbers, having a variable number of beds for one adsorber and a fixed number for the other, having a variable number of beds for both adsorbers.

In order to separate the raffinate-2 from the desorbent, a new distillation column (RAF-2) must also be installed. The top of the distillation column (RAF-2) will be isomerized in the isomerization unit (ISOM-1) preferentially in liquid phase as described above.

A second liquid-phase isomerization unit (ISOM-1) is added, the effluent from which will supply the simulated moving bed (SMB-2) preferentially without passing through the separation column (S-1) in order to avoid the addition of a second column for the separation of the xylenes.

Furthermore, an extraction column (EXT-2) must be added, supplied with the extract (12) from the separation unit (SMB-2).

Figure 2:
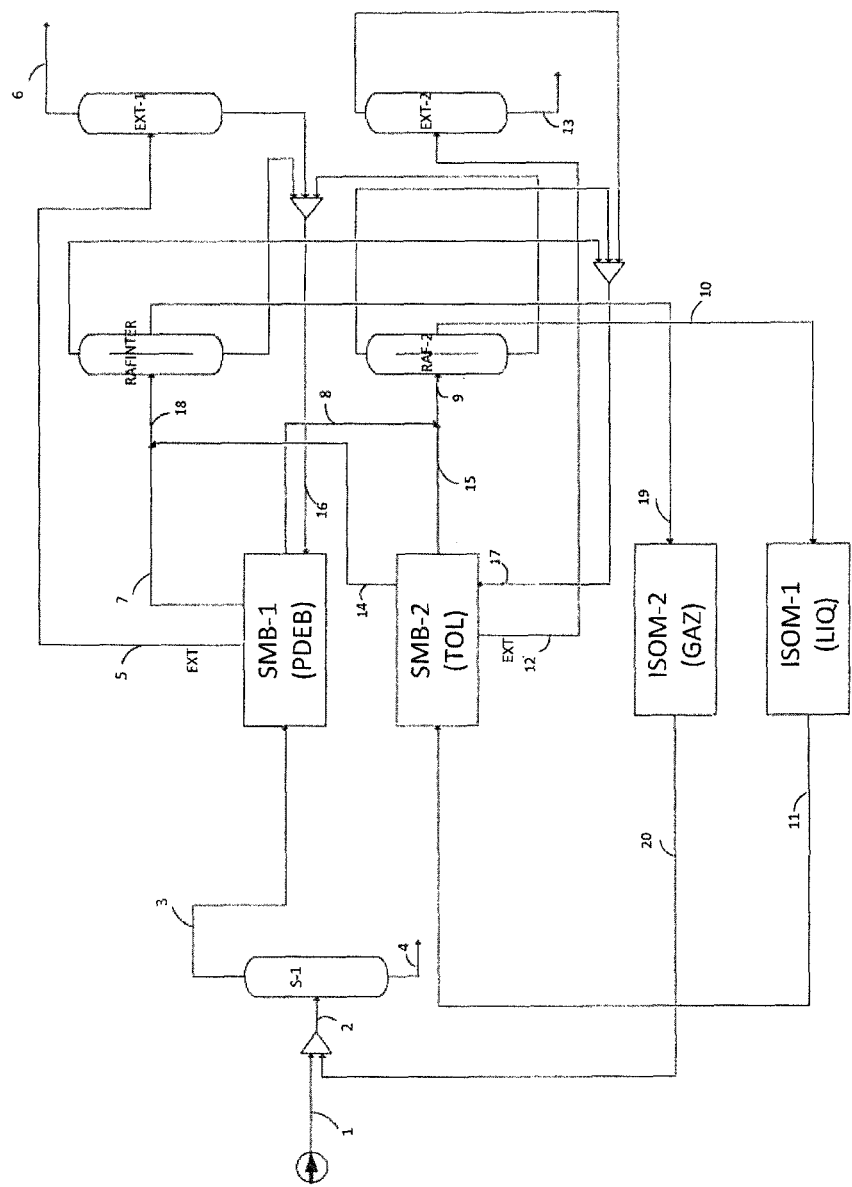
FIG. 2 shows a variant of the process according to the invention which results in the use of columns with walls known as "internal divided wall column".

FIG. 2 represents a variant of the layout of the process according to the invention that differs from that of FIG. 1 in that the separation unit (SMB-1) uses PDEB as desorbent and the separation unit (SMB-2) uses toluene. The intermediate raffinate flows (flows (7) and (14)) are mixed before the inlet of the distillation column (RAFINTER). In order to output the toluene at the top of the distillation column (RAFINTER) the PDEB at the bottom and the intermediate raffinate from which these desorbents have been removed on the side, a longitudinal division column known as a "dividing wall column" is required. A dividing wall column makes it possible to separate 3 high-purity compounds via a single column.

Optionally, the same applies to the distillation column (RAF-2) which is supplied by the raffinate-2 flows (flows (8) and (14)). In the event that the distillation column is not of the dividing wall type, only the paradiethylbenzene is output at the bottom of column in order to be recycled, the toluene being sent to the isomerization unit with the C8 aromatic cuts.

The fact of using two different desorbents in the two separation units (SMB-1 and SMB-2) has the advantage of avoiding the accumulation of aromatic impurities such as benzene and the heavy C9 and C10 aromatic compounds.

Using two different desorbents in the two separation units (SMB-1 and SMB-2) also makes it possible to carry out a thermal integration of the distillation columns (EXT-1 and EXT-2). In fact, the top of the distillation column (EXT-1) can potentially reboil all or part of the distillation column (EXT-2).

EXAMPLES

Example 1 According to the Prior Art

Figure 3:
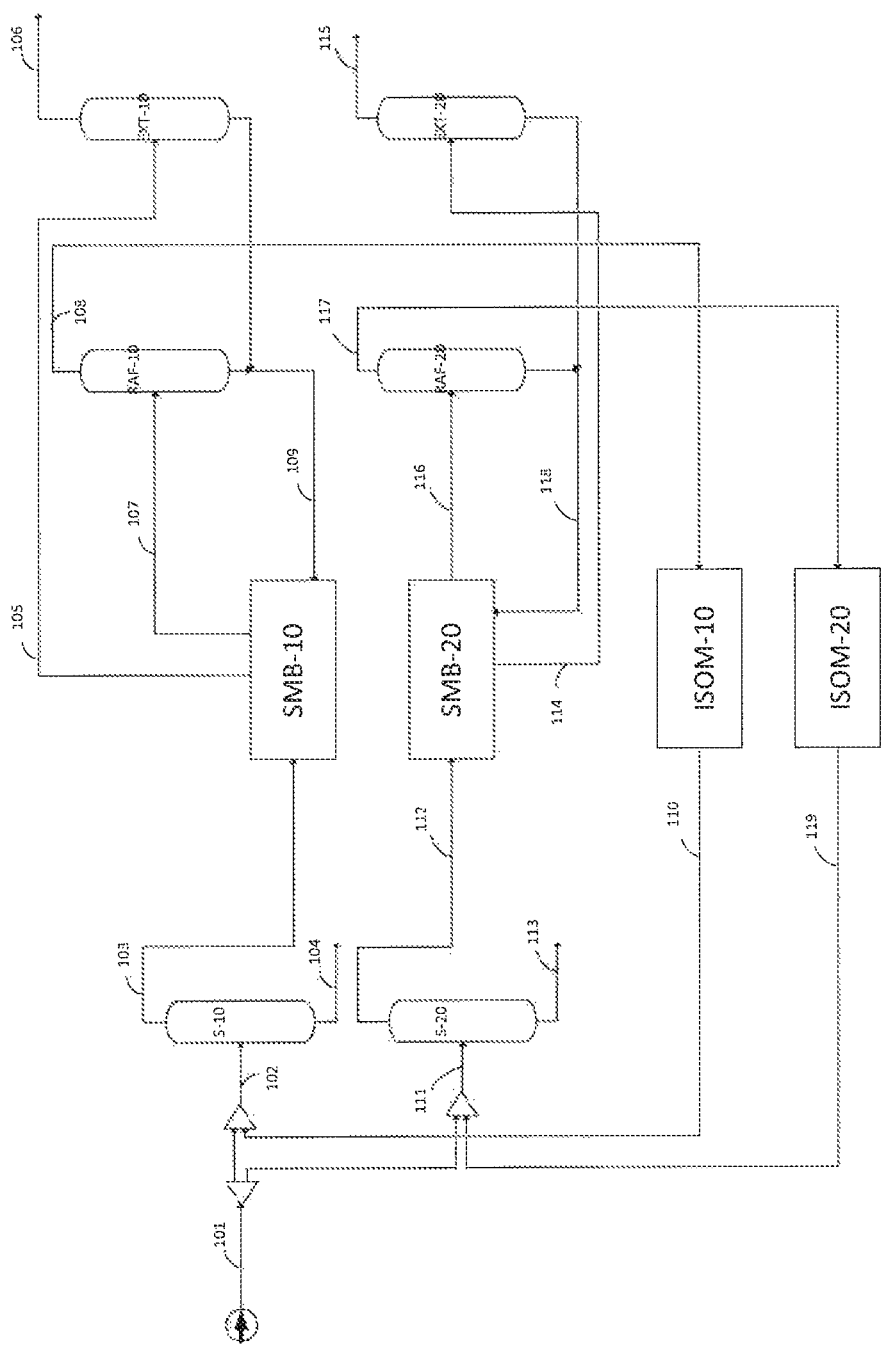
FIG. 3 shows a layout of the process according to the prior art which is used for Example 1.

This example illustrates the prior art and describes an aromatic complex constituted by two C8-aromatic loops in parallel, which are typical of the industrial complexes where the quantity of paraxylene produced is greater than the capacity that can be accepted by a single C8-aromatic loop, as shown in FIG. 3 and comprising:

two xylenes columns (S-10 and S-20) making it possible to extract the C9 and C10 aromatics (flow 104 and 113) and to send a flow (103) and a flow (112) essentially constituted by C8 aromatics to the adsorption units (SMB-10 and SMB-20), a first simulated moving bed adsorption unit (SMB-10) with 4 zones from which an extract (105) and a single raffinate (107) are drawn off, a first isomerization unit (ISOM-10) supplied with a part (108) of the raffinate (107) after elimination of the desorbent (109) by means of the distillation column (RAF-10), a first paraxylene extraction column (EXT-10) from which the desorbent which is recycled to the adsorption unit (SMB-1) via the flow (109) is drawn off at the bottom and a cut rich in paraxylene (106) is drawn off at the top, a second simulated moving bed adsorption unit (SMB-20) with 4 zones from which an extract (114) and a single raffinate (116) are drawn off, a second isomerization unit (ISOM-20) supplied with a part (117) of the raffinate (116) after elimination of the desorbent (118) by means of the distillation column (RAF-20), a second paraxylene extraction column (EXT-20) from which the desorbent which is recycled to the adsorption unit (SMB-2) via the flow (118) is drawn off at the bottom and a cut rich in paraxylene (115) is drawn off at the top.

The material balance of the process is described in Table 1 below.

Only the C8-aromatic and C9+ compounds are described, disregarding the other compounds and the formation of C9+ in the isomerization units. The unit used for the flow rate is kilotonne per year (kt/yr).

TABLE 1

|  |  | PX | EB | MOX | C9+ | Total |
|---|---|---|---|---|---|---|
| Fresh feedstock | 101 | 23.6 | 15.6 | 67.7 | 13.8 | 120.6 |
| S-10 feedstock | 102 | 50.0 | 22.9 | 148.5 | 6.9 | 228.3 |
| SMB-10 feedstock | 103 | 50.0 | 22.9 | 148.5 | 0 | 221.4 |
| S-10 bottom | 104 | 0 | 0 | 0 | 6.9 | 6.9 |
| EXT-10 top | 106 | 50.0 | 0 | 0 | 0 | 50.0 |
| ISOM-10 inlet | 108 | 0 | 22.9 | 148.5 | 0 | 171.4 |
| ISOM-10 outlet | 110 | 38.2 | 15.1 | 114.7 | 0 | 168.0 |
| S-20 feedstock | 111 | 50.0 | 22.9 | 148.5 | 6.9 | 228.3 |
| SMB-20 feedstock | 112 | 50.0 | 22.9 | 148.5 | 0 | 221.4 |
| S-20 bottom | 113 | 0 | 0 | 0 | 6.9 | 6.9 |
| EXT-20 top | 115 | 50.0 | 0 | 0 | 0 | 50.0 |
| ISOM-20 inlet | 117 | 0 | 22.9 | 148.5 | 0 | 171.4 |
| ISOM-20 outlet | 119 | 38.2 | 15.1 | 114.7 | 0 | 168.0 |

The feedstock (101) which supplies the aromatic loop (mixture of the heavy reformate and toluene-column bottoms) has a flow rate of 120.6 kt/yr. This feedstock is divided into two equal flows of 60.3 kt/yr. 168 kt/yr of isomerate (110) recycled from the isomerization unit (ISOM-10) is added to a first part of the feedstock (101) so as to isomerize the ethylbenzene. The resulting flow (102) is distilled in the xylenes column (S-10).

6.9 kt/yr of a mixture of C9 and C10 aromatics (104) is drawn off at the bottom of the column (S-10) and 221.4 kt/yr of a C8 aromatics cut (103) is drawn off at the top, of which the paraxylene content is 22.6%, the ethylbenzene content is 10.3% the orthoxylene and metaxylene content is 67.1%.

This cut is sent into a simulated moving bed adsorption unit with four zones (SMB-10) and four main flows: the feedstock (103), the desorbent (109), the extract (105) and the raffinate (107). This unit is composed of 12 beds containing an X zeolite exchanged with barium. The temperature is 175° C. The configuration is: 2 beds in zone 1, 5 beds in zone 2, 3 beds in zone 3 and 2 beds in zone 4. The solvent used is paradiethylbenzene.

The extract (105) at the outlet of the adsorption unit (SMB-10) is sent into a distillation column (EXT-10) from which the desorbent recycled to the adsorption unit (SMB-10) is drawn off at the bottom, and 50 kt/yr of a mixture (106), essentially constituted by toluene and paraxylene, is drawn off at the top.

The raffinate is sent into a distillation column (RAF-10) from which the desorbent recycled to the adsorption unit (SMB-10) is drawn off at the bottom, and 171.4 kt/yr of a mixture (108) is drawn off at the top.

This flow is sent into an isomerization unit (ISOM-10).

The isomerization unit (ISOM-10) operates in gas phase under the following conditions:
Temperature: 385° C.
Catalyst: contains platinum and EU-1 zeolite
Hourly space velocity: 3.5 h$^{-1}$
H2/hydrocarbon ratio: 4.4:1
Pressure: 0.9 MPa The ethylbenzene content of the mixture introduced into the isomerization unit (ISOM-10) is 13.4%. A 2% loss by cracking is observed in this isomerization, i.e. a flow rate of 3.4 kt/yr. The ethylbenzene is partially isomerized, 9% of it remains in the outlet flow (110).

This isomerate (110) has a flow rate of 168 kt/yr; it is recycled to the inlet of the S-10 column where it is mixed with a part of the fresh feedstock (101) which has a flow rate of 60.3 kt/yr.

168 kt/yr of isomerate (119) recycled from the isomerization unit (ISOM-20) is added to a first part of the feedstock (101) so as to isomerize the ethylbenzene. The resulting flow (111) is distilled in the xylenes column (S-20).

6.9 kt/yr of a mixture of C9 and C10 aromatics (flow 113) is drawn off at the bottom of the column (S-20) and 221.4 kt/yr of a C8 aromatics cut (flow 112) is drawn off at the top, of which the paraxylene content is 22.6%, and the ethylbenzene content is 10.4%.

This cut is sent into a simulated moving bed adsorption unit with four zones (SMB-20) and four main flows: the feedstock (flow 112), the desorbent (flow 118), the extract (flow 114) and the raffinate (flow 116). This unit is composed of 12 beds containing an X zeolite exchanged with barium. The temperature is 175° C. The configuration is: 2 beds in zone 1, 5 beds in zone 2, 3 beds in zone 3 and 2 beds in zone 4. The solvent used is paradiethylbenzene.

The extract (114) at the outlet of the adsorption unit (SMB-20) is sent into a distillation column (EXT-20) from which the desorbent recycled to the adsorption unit (SMB-20) is drawn off at the bottom and 50 kt/yr of a mixture (115) essentially constituted by toluene and paraxylene is drawn off at the top.

The raffinate is sent into a distillation column (RAF-20) from which the desorbent recycled to the adsorption unit (SMB-20) is drawn off at the bottom, and 171.4 kt/yr of a mixture (117) is drawn off at the top.

This flow is sent into an isomerization unit (ISOM-20). The isomerate obtained (119) is recycle to the inlet of the column S-20 where it is mixed with a part of the fresh feedstock (101).

The isomerization unit (ISOM-20) operates in gas phase under the following conditions:
Temperature: 385° C.
Catalyst: contains platinum and EU-1 zeolite
Hourly space velocity: 3.5 h$^{-1}$
H2/hydrocarbon ratio: 4.4:1
Pressure: 0.9 MPa The ethylbenzene content of the mixture introduced into the isomerization unit (ISOM-20) is 13.4%.

A 2% loss by cracking is observed in this isomerization, i.e. a flow rate of 3.4 kt/yr. The ethylbenzene is partially isomerized. 9% of it remains in the outlet flow (119).

This isomerate (119) has a flow rate of 168 kt/yr. It is recycled to the inlet of the column S-20 where it is mixed with a part of the fresh feedstock (101) which has a flow rate of 60.3 kt/yr.

Example 2 According to the Invention

This example illustrates the process according to the invention and describes the aromatic loop shown in FIG. 1 and comprising:
- a xylenes column (S-1) making it possible to extract the C9 and C10 aromatics (4) and to send a flow (3) essentially constituted by C8 aromatics to the adsorption unit (SMB-1),
- a first simulated moving bed adsorption unit (SMB-1) with 5 zones from which an extract (5), an intermediate raffinate (7) and a raffinate-2 (8) are drawn off,
- a first paraxylene extraction column (EXT-1) from which the desorbent which is recycled to the adsorption units (SMB-1 and SMB-2) via the flows (16) and (17) is drawn off at the bottom and a cut rich in paraxylene (flow 6) is drawn off at the top,
- a second simulated moving bed adsorption unit (SMB-2) with 5 zones of from which an extract (12), an intermediate raffinate (14) and a raffinate-2 (15) are drawn off,
- a second paraxylene extraction column (EXT-2) from which the desorbent which is recycled to the adsorption units (SMB-1 and SMB-2) via the flows (16) and (17) is drawn off at the bottom and a cut rich in paraxylene (flow 13) is drawn off at the top,
- a first isomerization unit (ISOM-1) supplied by a part (10) of the raffinate-2 (9) constituted by the mixture of the flows (8) and (15) after elimination of the desorbent by means of the distillation column (RAF-2),
- a second isomerization unit (ISOM-2) supplied by a part (19) of the intermediate raffinate (18) constituted by the mixture of the flows (7) and (14) after elimination of the desorbent by means of the distillation column (RAFINTER).

The material balance of the process is described in Table 2 below. Only the C8-aromatic and C9+ compounds are described; the other compounds and the formation of C9+ in the isomerization units are disregarded. The unit used for the flow rate is kilotonne per year (kt/yr).

TABLE 2

|  |  | PX | EB | MOX | C9+ | Total |
|---|---|---|---|---|---|---|
| Fresh feedstock | 1 | 22.6 | 15.2 | 64.7 | 13.2 | 115.8 |
| S-1 feedstock | 2 | 51.1 | 26.5 | 150.4 | 13.2 | 241.2 |
| SMB-1 feedstock | 3 | 51.1 | 26.5 | 150.4 | 0 | 228.0 |
| S-1 bottom | 4 | 0 | 0 | 0 | 13.2 | 13.2 |
| EXT-1 top | 6 | 51.1 | 0 | 0 | 0 | 51.1 |
| RAFF INTER | 7 | 0 | 15.9 | 50.4 | 0 | 66.3 |
| RAFF-2 | 8 | 0 | 10.6 | 100.0 | 0 | 110.6 |
| ISOM LIQ inlet | 10 | 0 | 17.7 | 195.6 | 0 | 213.3 |
| ISOM LIQ outlet | 11 | 48.9 | 17.7 | 146.7 | 0 | 213.3 |
| Top EXT-2 | 13 | 48.9 | 0 | 0 | 0 | 48.9 |
| RAFF-INTER | 14 | 0 | 10.6 | 51.0 | 0 | 61.7 |
| RAFF-2 | 15 | 0 | 7.1 | 95.7 | 0 | 102.8 |
| ISOM GAS inlet | 19 | 0 | 26.5 | 101.5 | 0 | 128.0 |
| ISOM GAS outlet | 20 | 28.5 | 11.3 | 85.6 | 0 | 125.4 |

The fresh feedstock (1) which supplies the aromatic loop has a flow rate of 115.8 kt/yr.

125.4 kt/yr of isomerate (20) recycled from the isomerization unit (ISOM-2) is added to this feedstock isomerizing the ethylbenzene. The resulting flow (2) is distilled in the xylenes column (S-1).

13.2 kt/yr of a mixture of C9 and C10 aromatics (4) is drawn off at the bottom of the column (S-1) and 228 kt/yr of a cut of C8 aromatics (3) is drawn off at the top, of which the paraxylene content is approximately 22.4%, the ethylbenzene content is approximately 11.6% the content of orthoxylene and metaxylene is approximately 65.9%.

This cut is sent into a simulated moving bed adsorption unit with five zones (SMB-1) and five main flows: the feedstock (3), the desorbent (16), the extract (5), the intermediate raffinate (7) and the raffinate-2 (8). This unit is composed of 12 beds containing an X zeolite exchanged with barium. The temperature is 175° C. The configuration is: 2 beds in zone 1, 5 beds in zone 2, 2 beds in zone 3A, 2 beds in zone 3B and one bed in zone 4. The solvent used is paradiethylbenzene.

The extract (5) at the outlet of the adsorption unit (SMB-1) is sent into a distillation column (EXT-1) from which the desorbent recycled to the adsorption unit (SMB-1) is drawn off at the bottom, and 51.1 kt/yr of a mixture (6) essentially constituted by toluene and paraxylene is drawn off at the top.

The isomerate (11) originating from the isomerization unit (ISOM-1) supplies a second simulated moving bed adsorption unit with five zones (SMB-2) and five main flows: the feedstock (11), the desorbent (17), the extract (12), the intermediate raffinate (14) and the raffinate-2 (15). This unit is composed of 12 beds containing an X zeolite exchanged with barium.

The temperature is 175° C.

The configuration is: 2 beds in zone 1, 5 beds in zone 2, 2 beds in zone 3A, 2 beds in zone 3B and one bed in zone 4. The solvent used is paradiethylbenzene.

The extract (12) at the outlet of the adsorption unit (SMB-2) is sent into a distillation column (EXT-2) from which the desorbent recycled to the adsorption unit (SMB-2) is drawn off at the bottom, and 48.9 kt/yr of a mixture (13) essentially constituted by toluene and paraxylene is drawn off at the top.

The raffinates-2 denoted (8) and (15), are mixed and sent into a distillation column (RAF-2) from which the desorbent recycled to the adsorption units (SMB-1 and SMB-2) is drawn off at the bottom, and 213.3 kt/yr of a mixture (10) is drawn off at the top.

This flow is sent into an isomerization unit (ISOM-1).

The isomerization unit (ISOM-1) operates in liquid phase under the following conditions:
Temperature: 240° C.
Catalyst: contains ZSM-5 zeolite
Hourly space velocity: 3 h$^{-1}$
Pressure: 1.9 MPa The ethylbenzene content of the mixture introduced into the isomerization unit (ISOM-1) is approximately 8.3%. The ethylbenzene is not converted; the quantity thereof is therefore the same in the outlet flow (11). This isomerate (11) has a flow rate of 213.3 kt/yr; it is recycled to the inlet of the adsorption unit (SMB-2) without passing through the column (S-1).

The intermediate raffinates (7) and (14) are mixed and sent into a distillation column (RAFINTER) from which the desorbent recycled to the adsorption units (SMB-1 and SMB-2) is drawn off at the bottom, and 128 kt/yr of a mixture (19) is drawn off at the top.

This flow is sent into an isomerization unit (ISOM-2).

The isomerization unit (ISOM-2) operates in gas phase under the following conditions:
Temperature: 385° C.
Catalyst: contains platinum and EU-1 zeolite
Hourly space velocity: 3.5 h$^{-1}$
Pressure: 0.9 MPa The ethylbenzene content of the mixture introduced into the isomerization unit (ISOM-2) is 20.7%. A 2% loss by cracking is observed in this isomerization, i.e. a flow rate of 2.6 kt/yr. The ethylbenzene is partially isomerized; 9% of it remains in the outlet flow (20).

This isomerate (20) has a flow rate of 125.4 kt/yr; it is recycled to the inlet of the column S-1 where it is mixed with the fresh feedstock (1) which has a flow rate of 115.8 kt/yr.

The invention has several advantages compared with the prior art. Firstly, the liquid-phase isomerization consumes less energy than gas-phase isomerization. In fact, it operates at a lower temperature. It also operates without hydrogen recycling, therefore without a recycling compressor. Finally, it produces a much lower quantity of by-products, in particular of the C9 aromatics, which makes it possible to by-pass the C9 aromatics elimination column (S-1) greatly reducing the energy required for this separation.

The invention claimed is:

1. A process for producing high-purity paraxylene from a xylenes cut containing ethylbenzene and C9+ compounds, which process is performed in an apparatus that contains two simulated moving bed separation units (SMB-1 and SMB-2), and two isomerization units (ISOM-1 and ISOM-2), wherein ISOM-1 operates in liquid phase and ISOM-2 operates in gas phase, said process consisting of the following series of stages:
sending a feedstock (2) comprising metaxylene, paraxylene, orthoxylene, ethylbenzene, and C9+ compounds to a distillation column (S-1) from where a mixture (3) is drawn off at a top comprising a major part of the metaxylene, paraxylene, and ethylbenzene, and at least a part of the orthoxylene, and from where a flow (4) of C9-C10 hydrocarbons and the remaining part of the orthoxylene is drawn off at a bottom,
separating the mixture from the top (3) in the separation unit (SMB-1) comprising at least one adsorber containing a plurality of interconnected beds and operating in a closed loop, said adsorber comprising at least five zones delimited by injections of the mixture (3) and a first desorbent (16), and draw-offs of a first extract (5) containing paraxylene, a first intermediate raffinate (7) containing ethylbenzene, and a first raffinate-2 (8) containing orthoxylene and metaxylene,
carrying out a simulated moving bed separation of a first isomerate (11) originating from the isomerization unit (ISOM-1) in the separation unit (SMB-2) constituted by at least one adsorber containing a plurality of interconnected beds and operating optionally in a closed loop, said adsorber comprising at least five zones delimited by injections of the first isomerate (11) and of a second desorbent (17), and draw-offs of a second extract (12) containing paraxylene, a second intermediate raffinate (14) containing ethylbenzene, and a second raffinate-2 (15) containing orthoxylene and metaxylene,
recovering a paraxylene-enriched fraction from the first extract (5) and/or the second extract (12),
mixing the first and second raffinates-2 (8) and (15) to form a flow (9) which is distilled in a column (RAF-2) to eliminate substantially all of the desorbents (16) and (17) and to draw off a first distilled fraction (10),
supplying the isomerization unit (ISOM-1) with the first distilled fraction (10) to obtain the first isomerate (11),
mixing the first and second intermediate raffinates (7) and (14) to form a flow (18) which is distilled in a column (RAFINTER) to substantially eliminate all of the desorbents (16) and (17) and to draw off a second distilled fraction (19),
supplying the isomerization unit (ISOM-2) with the second distilled fraction (19) to obtain a second isomerate (20), which is recycled to an inlet of the separation column (S-1).

2. The process for the production of high-purity paraxylene from a xylenes cut containing ethylbenzene and C9+ compounds according to claim 1, in which the isomerization unit (ISOM-1) operates in liquid phase under the following conditions:
a temperature less than 300° C.,
a pressure less than 4 MPa,
an hourly space velocity less than 10 h$^{-1}$, in the presence of a catalyst comprising at least one zeolite having channels the opening of which is defined by a ring with 10 or 12 oxygen atoms (10 MR or 12 MR).

3. The process for the production of high-purity paraxylene from a xylenes cut containing ethylbenzene and C9+ compounds according to claim 1, in which the isomerization unit (ISOM-2) operates in liquid phase under the following conditions:
 a temperature greater than 300° C.,
 a pressure less than 2.5 MPa,
 an hourly space velocity less than 10 $h^{-1}$,
 a hydrogen to hydrocarbon molar ratio less than 10.

4. The process for the production of high-purity paraxylene from a xylenes cut containing ethylbenzene and C9+ compounds according to claim 3, in which the catalyst for the isomerization unit (ISOM-2) contains an acid zeolite, and at least one metal of group VIII of the periodic table.

5. The process for the production of high-purity paraxylene from a xylenes cut containing ethylbenzene and C9+ compounds according to claim 3, in which the catalyst for the isomerization unit (ISOM-2) contains at least one zeolite having channels the opening of which is defined by a ring with 10 to 12 oxygen atoms (10 MR or 12 MR), and at least one group VIII metal at a content between 0.1 and 0.3% by weight, inclusive.

6. The process for the production of high-purity paraxylene from a xylenes cut containing ethylbenzene and C9+ compounds according to claim 1, in which the separation unit (SMB-1) contains PDEB as desorbent.

7. The process for the production of high-purity paraxylene from a xylenes cut containing ethylbenzene and C9+ compounds according to claim 1, in which the separation unit (SMB-2) contains toluene as desorbent.

8. The process for the production of high-purity paraxylene from a xylenes cut containing ethylbenzene and C9+ compounds according to claim 1, in which the separation units (SMB1) and (SMB-2) contain from 6 to 24 beds, distributed over one or more adsorbers, the number of beds being adjusted so that each bed optionally has a height between 0.70 m and 1.40 m.

9. The process for the production of high-purity paraxylene from a xylenes cut containing ethylbenzene and C9+ compounds according to claim 1, in which the distribution of the quantity of solid adsorbent in the separation units (SMB-1) and (SMB-2) is as follows:
 the quantity of solid adsorbent in a zone 1 is 16%±5%,
 the quantity of solid adsorbent in a zone 2 is 40%±5%,
 the quantity of solid adsorbent in a zone 3A is 16%±5%,
 the quantity of solid adsorbent in a zone 3B is 16%±5%,
 the quantity of solid adsorbent in a zone 4 is 12%±5%,
 wherein the zones are as follows:
 zone 1 is between the injection of the desorbent and the draw off of the extract,
 zone 2 is between the draw-off of the extract and the injection of the feedstock,
 zone 3A is between the injection of the feedstock and the draw-off of the intermediate raffinate,
 zone 3B is between the draw off of the intermediate raffinate and the draw-off of the raffinate-2,
 zone 4 is between the draw-off of the raffinate-2 and the injection of the desorbent.

10. The process for the production of high-purity paraxylene from a xylenes cut containing ethylbenzene and C9+ compounds according to claim 1, in which, with respect to the separation unit (SMB-1), a ratio by volume of desorbent to feedstock is at least 1.7/1.

11. The process for the production of high-purity paraxylene from a xylenes cut containing ethylbenzene and C9+ compounds according to claim 1, in which, with respect to the separation unit (SMB-1), a ratio of flow rates of intermediate raffinate and raffinate-2 is between 0.3/1 and 5/1, inclusive.

12. The process for the production of high-purity paraxylene from a xylenes cut containing ethylbenzene and C9+ compounds according to claim 1, in which, with respect to the separation unit (SMB-2), a ratio by volume of desorbent to feedstock is at least 1.7/1.

13. The process for the production of high-purity paraxylene from a xylenes cut containing ethylbenzene and C9+ compounds according to claim 1, in which, with respect to the separation unit (SMB-2), a ratio of flow rates of intermediate raffinate and raffinate-2 is between 0.3/1 and 5/1, inclusive.

14. The process for the production of high-purity paraxylene from a xylenes cut containing ethylbenzene and C9+ compounds according to claim 1, which is a process based on debottlenecking of an existing separation unit, constituted by two adsorbers in series, as follows:
 the last bed of the first adsorber is connected to the first bed of the first adsorber via a line containing at least one recirculation pump, this first adsorber acting as a separation unit (SMB-1), and
 the last bed of the second adsorber is connected to the first bed of the second adsorber via a line containing at least one recirculation pump, this second adsorber acting as a separation unit (SMB-2).

15. The process for the production of high-purity paraxylene from a xylenes cut containing ethylbenzene and C9+ compounds according to claim 1, in which the configuration of the two separation units (SMB-1) and (SMB-2) has a fixed number of beds in each of the chromatographic zones of each of the two separation units.

16. The process for the production of high-purity paraxylene from a xylenes cut containing ethylbenzene and C9+ compounds according to claim 1, in which:
 the first extract (5) originating from the separation unit (SMB-1) is distilled in a column (EXT-1) to recover a first fraction (6) enriched with paraxylene, and
 the second extract (12) is distilled in a column (EXT 2) to recover a second fraction (13) enriched with paraxylene.

17. The process for the production of high-purity paraxylene from a xylenes cut containing ethylbenzene and C9+ compounds according to claim 1, in which the two extracts (5) and (12) are distilled in a single common extraction column in order to recover a single fraction enriched with paraxylene.

18. The process for the production of high-purity paraxylene from a xylenes cut containing ethylbenzene and C9+ compounds according to claim 1, wherein the column (RAFINTER) receives a mixture of two different desorbents, one from SMB-1 and another from SMB-2 and the column (RAF-2) receives a mixture of two different desorbents, one from SMB-1 and another from SMB-2.

19. The process for the production of high-purity paraxylene from a xylenes cut containing ethylbenzene and C9+ compounds according to claim 1, in which the isomerization unit (ISOM-1) operates in liquid phase under the following conditions:
 a temperature of 200 to 260° C.,
 a pressure of 2 to 3 MPa,
 an hourly space velocity of 2 $h^{-1}$ to 4 $h^{-1}$, in the presence of a catalyst comprising at least one zeolite having channels the opening of which is defined by a ring with 10 oxygen atoms (10 MR).

20. The process for the production of high-purity paraxylene from a xylenes cut containing ethylbenzene and C9+ compounds according to claim 1, in which the isomerization unit (ISOM-2) operates in liquid phase under the following conditions:
   a temperature of 360° C. to 480° C.,
   a pressure of 0.5 to 0.8 MPa,
   an hourly space velocity of 0.5 $h^{-1}$ to 6 $h^{-1}$,
   a hydrogen to hydrocarbon molar ratio of 3 to 6.

\* \* \* \* \*